(12) United States Patent
Truckai et al.

(10) Patent No.: US 8,460,292 B2
(45) Date of Patent: *Jun. 11, 2013

(54) ELECTROSURGICAL INSTRUMENT AND METHOD

(75) Inventors: Csaba Truckai, Saratoga, CA (US); John H. Shadduck, Menlo Park, CA (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/323,032

(22) Filed: Dec. 12, 2011

(65) Prior Publication Data

US 2012/0136352 A1 May 31, 2012

Related U.S. Application Data

(60) Division of application No. 11/173,878, filed on Jul. 2, 2005, now Pat. No. 8,075,558, which is a continuation-in-part of application No. 10/136,874, filed on Apr. 30, 2002, now Pat. No. 6,913,579.

(51) Int. Cl.
*A61B 18/14* (2006.01)

(52) U.S. Cl.
USPC .............................................. 606/51; 606/171

(58) Field of Classification Search
USPC .................................................... 606/51, 171
See application file for complete search history.

(56) References Cited

U.S. PATENT DOCUMENTS

| | | | |
|---|---|---|---|
| 659,409 A | 10/1900 | Mosher | |
| 1,586,645 A | 6/1926 | Bierman | |
| 1,798,902 A | 3/1931 | Raney | |
| 1,881,250 A | 10/1932 | Tomlinson | |
| 2,031,682 A | 2/1936 | Wappler et al. | |
| 3,685,518 A | 8/1972 | Beuerle et al. | |
| 3,730,188 A | 5/1973 | Ellman | |
| 4,237,441 A | 12/1980 | Van Konynenburg et al. | |
| 4,304,987 A | 12/1981 | Van Konynenburg | |
| 4,545,926 A | 10/1985 | Fouts, Jr. et al. | |
| 4,849,133 A | 7/1989 | Yoshida et al. | |
| 4,910,389 A | 3/1990 | Sherman et al. | |
| 5,106,538 A | 4/1992 | Barma et al. | |
| 5,716,366 A | 2/1998 | Yates | |
| 5,880,668 A | 3/1999 | Hall | |
| 6,913,579 B2 * | 7/2005 | Truckai et al. ................. 600/564 |
| 6,929,644 B2 | 8/2005 | Truckai et al. | |
| 7,041,102 B2 | 5/2006 | Truckai et al. | |
| 7,112,201 B2 | 9/2006 | Truckai et al. | |
| 7,169,146 B2 | 1/2007 | Truckai et al. | |
| 8,075,558 B2 * | 12/2011 | Truckai et al. .................. 606/51 |
| 2006/0000823 A1 | 1/2006 | Truckai et al. | |

FOREIGN PATENT DOCUMENTS

EP          0730282 A2          9/1996

\* cited by examiner

*Primary Examiner* — Lee S Cohen

(57) ABSTRACT

An electrosurgical working end and method for sealing and transecting tissue. An exemplary working end provides curved jaw members that are positioned on opposing sides of the targeted anatomic structure. The working end carries a slidable extension member having flange portions with inner surfaces that slide over the jaw members to clamp tissue therebetween. The working end carries an independent slidable cutting member that is flexible to follow the curved axis of the jaws. The electrosurgical surfaces of the jaws include partially-resistive bodies for carrying a current or load which modulates ohmic heating in the engaged tissue to prevent charring and desiccation of tissue to create a high strength thermal seal.

17 Claims, 17 Drawing Sheets

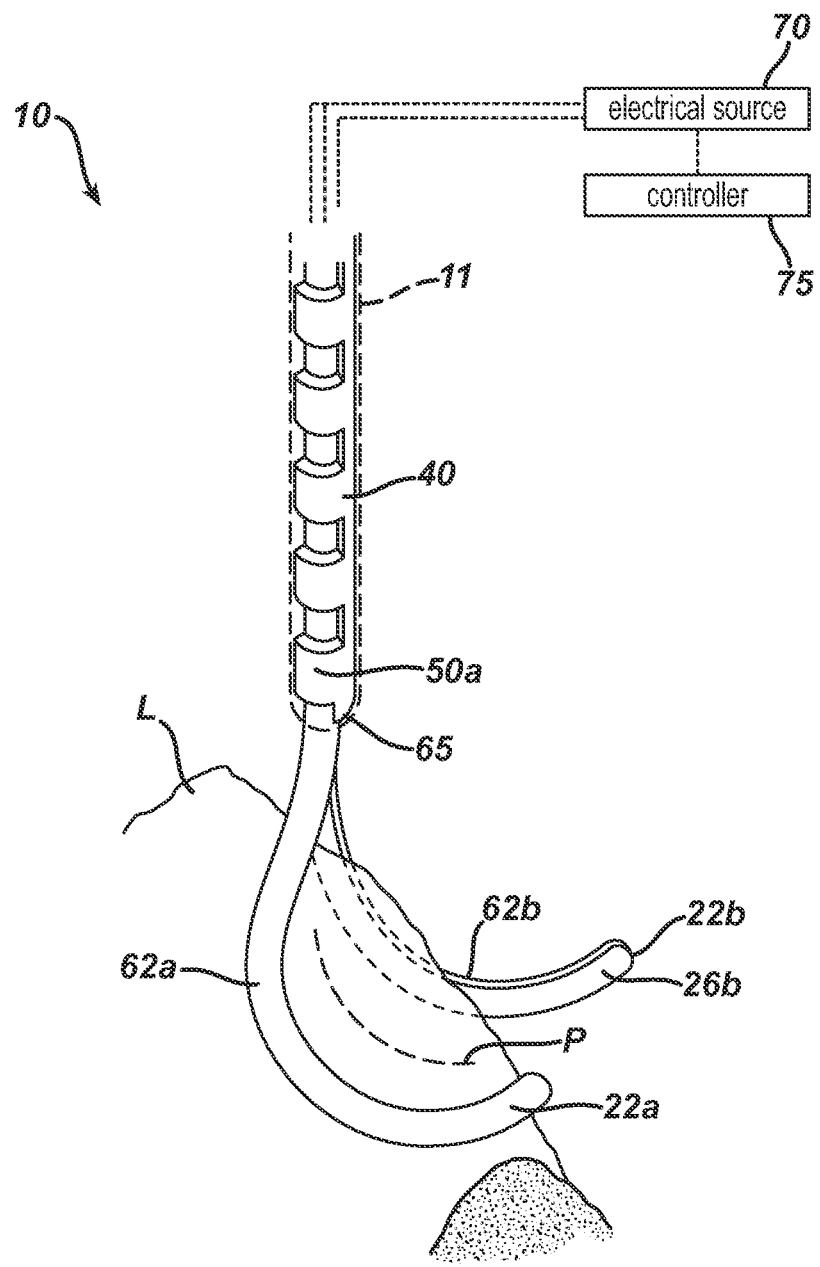

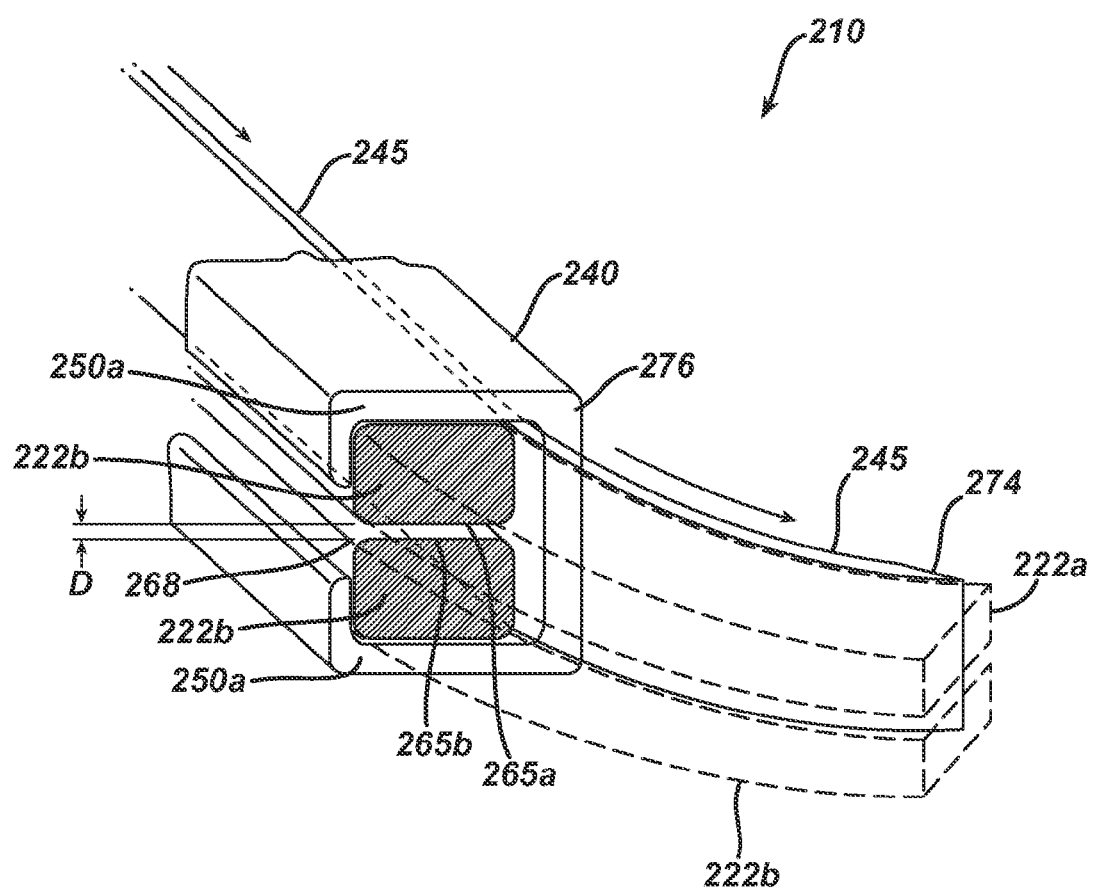

ELECTROSURGICAL INSTRUMENT AND METHOD

CROSS-REFERENCE TO RELATED APPLICATIONS

This application claims priority to and is a divisional of U.S. patent application Ser. No. 11/173,878, filed on Jul. 2, 2005, now U.S. Pat. No. 8,075,558, which a Continuation-in-Part of U.S. patent application Ser. No. 10/136,874 filed Apr. 30, 2002, now U.S. Pat. No. 6,913,579. This application also is related to the following co-pending U.S. patent application Ser. No. 10/032,867 filed Oct. 22, 2001, now U.S. Pat. No. 6,929,644, Ser. No. 10/308,362 filed Dec. 3, 2002 now U.S. Pat. No. 6,770,072, and Ser. No. 10/291,286 filed Nov. 9, 2002, now U.S. Pat. No. 6,926,716. The entire contents of the above-listed patent applications are incorporated herein by this reference and should be considered a part of this specification.

FIELD OF THE INVENTION

This invention relates to medical devices and techniques and more particularly relates to the working end of an electrosurgical instrument that is adapted for sealing and transecting tissue.

BACKGROUND OF THE INVENTION

In various open and laparoscopic surgeries, it is necessary to seal or weld the margins of transected tissue volumes and transected blood vessels. However, satisfactory instruments have not been developed for electrosurgically excising a tissue biopsy sample from a lung or liver, for example, that seal the margin of the targeted structure while at the same time preventing gross thermal damage to the resected tissue sample.

As background, various radiofrequency (Rf) surgical instruments have been developed for sealing the edges of transected tissues. For example, FIG. 1A shows a sectional view of paired electrode jaws 2a and 2b of a typical prior art bi-polar Rf grasper grasping two tissue layers. In a typical bi-polar jaw arrangement, each jaw face comprises an electrode and Rf current flows across the tissue between the first and second polarities in the opposing jaws that engage opposing exterior surfaces of the tissue. FIG. 1A shows typical lines of bi-polar current flow between the jaws. Each jaw in FIG. 1A has a central slot adapted to receive a reciprocating blade member as is known in the art for transecting the captured vessel after it is sealed.

While bi-polar graspers as in FIG. 1A can adequately seal or weld tissue volumes that have a small cross-section, such bi-polar instruments are often ineffective in sealing or welding many types of anatomic structures, e.g., (i) anatomic structures having walls with irregular or thick fibrous content, such as lung tissue; (ii) bundles of disparate anatomic structures, and (iii) substantially thick anatomic and structures.

As depicted in FIG. 1A, a prior art grasper-type instrument is depicted with jaw-electrodes engaging opposing side of a tissue volume with substantially thick, dense and non-uniform fascia layers underlying its exterior surface. As depicted in FIG. 1A, the fascia layers f prevent a uniform flow of current from the first exterior tissue surface s to the second exterior tissue surface s that are in contact with electrodes 2a and 2b. The lack of uniform bi-polar current across the fascia layers f causes non-uniform thermal effects that typically result in localized tissue desiccation and charring indicated at c. Such tissue charring can elevate impedance levels in the captured tissue so that current flow across the tissue is terminated altogether. FIG. 1B depicts an exemplary result of attempting to create a weld across tissue with thick fascia layers f with a prior art bi-polar instrument. FIGS. 1A-1B show localized surface charring c and non-uniform weld regions w in the medial layers m of vessel. Further, FIG. 1B depicts a common undesirable characteristic of prior art welding wherein thermal effects propagate laterally from the targeted tissue causing unwanted collateral (thermal) damage indicated at d.

What is needed is an instrument working end that can utilize Rf energy (i) to transect tissue about a curved path; (ii) to provide a seal in tissue that limits collateral thermal damage; and (iii) to provide a seal or weld in substantially thick anatomic structures and tissue volumes that are not uniform in hydration, density and collagenous content.

SUMMARY OF THE INVENTION

The object of the present invention is to provide an instrument working end capable of transecting and compressing tissue to allow for controlled Rf energy delivery to transected tissue margins that have thick fascia layers or other tissue layers with non-uniform fibrous content. Such tissues are difficult to seal since the fascia layers can prevent uniform current flow and uniform ohmic heating of the tissue.

As background, the biological mechanisms underlying tissue fusion by means of thermal effects are not fully understood. In general, the delivery of Rf energy to a captured tissue volume elevates the tissue temperature and thereby at least partially denatures proteins in the tissue. The objective is to denature such proteins, including collagen, into a proteinaceous amalgam that intermixes and fuses together as the proteins renature. As the treated region heals over time, the biological weld is reabsorbed by the body's wound healing process.

In order to create an effective weld in a tissue volume dominated by the fascia layers, it has been found that several factors are critical. The objective is to create a substantially even temperature distribution across the targeted tissue volume to thereby create a uniform weld or seal. Fibrous tissue layers (i.e., fascia) conduct Rf current differently than adjacent less-fibrous layers, and it is believed that differences in extracellular fluid contents in such adjacent tissues contribute greatly to the differences in ohmic heating. It has been found that by applying high compressive forces to fascia layers and underlying non-fibrous layers, the extracellular fluids migrate from the site to collateral regions. Thus, the compressive forces can make resistance more uniform regionally within engaged tissue.

Another aspect of the invention provides means for creating high compression forces along the very elongate working end of the invention that engages the targeted tissue. This is accomplished by providing a slidable or translatable extension member that defines cam surfaces that engage the entire length of jaw members as the translatable member is extended over the jaws. The translatable member of the invention thus is adapted to perform multiple functions including contemporaneously closing the jaws and transecting the engaged tissue, applying very high compression to the engaged tissue, and cooperating with electrosurgical components of the jaws to deliver thermal energy to the engaged tissue.

The combination of the translatable extension member in cooperation with the curved jaws thus allows for electrosurgical electrode arrangements that are adapted for controlled application of current to engaged tissue. An exemplary electrosurgical instrument includes an openable-closeable jaw assembly with first and second jaw members with electrosurgical energy-delivery surfaces, wherein each jaw includes an opposing polarity conductive body coupled to an electrical source, and wherein at least one jaw surface includes a partially resistive body selected from the class consisting of a body having a fixed resistance, a body having resistance that changes in response to pressure and a body having resistance that changes in response to temperature. In these embodiments, the partially resistive body capable is of load-carrying to prevent arcing in tissue about the energy-delivery surfaces to create and effective weld without charring or desiccation of tissue.

In another embodiment of the invention, the working end includes components of a sensor system which together with a power controller can control Rf energy delivery during a tissue welding procedure. For example, feedback circuitry for measuring temperatures at one or more temperature sensors in the working end may be provided. Another type of feedback circuitry may be provided for measuring the impedance of tissue engaged between various active electrodes carried by the working end. The power controller may continuously modulate and control Rf delivery in order to achieve (or maintain) a particular parameter such as a particular temperature in tissue, an average of temperatures measured among multiple sensors, a temperature profile (change in energy delivery over time), or a particular impedance level or range.

Additional objects and advantages of the invention will be apparent from the following description, the accompanying drawings and the appended claims.

BRIEF DESCRIPTION OF THE DRAWINGS

Other objects and advantages of the present invention will be understood by reference to the following detailed description of the invention when considered in combination with the accompanying Figures, in which like reference numerals are used to identify like components throughout this disclosure.

FIGS. 4A-4C are illustrations of the steps of practicing the method of the invention with the working end of FIG. 2:

FIG. 4A depicting the positioning of the paired jaws over a targeted portion of a patient's lung;

FIG. 4B depicting the advancement of the translatable member over the jaw members to (i) transect the tissue to provide a biopsy sample and (ii) compressing the remaining tissue margin tightly between the jaw members for electrosurgical sealing; and FIG. 4C providing a sectional view taken along line 4C-4C of FIG. 4B to illustrate the path of Rf current flow through medial layers of the captured tissue.

FIG. 7A depicting a translatable member for closing the jaws in a non-extended position; FIG. 7B depicting the translatable member in an extended position that closes the jaws; and FIG. 7C depicting a blade member in an extended position to cut tissue engaged by the jaws.

FIG. 8B is a cut-away view of the working end of FIGS. 7A-7C with the cutting member in an extended position for cutting tissue.

DETAILED DESCRIPTION OF THE INVENTION

Figure 1A:
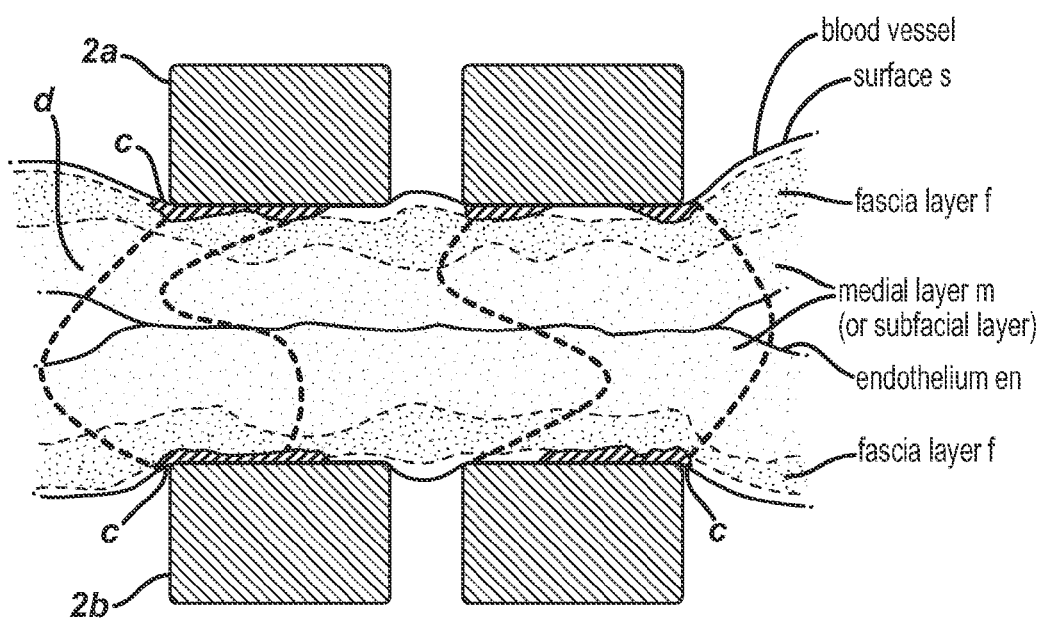
FIG. 1A is an illustration of current flow between the paired jaws of a prior art bi-polar radiofrequency device in a method of sealing a tissue with fascia layers that are resistant to Rf current flow therethrough.
Figure 1B:
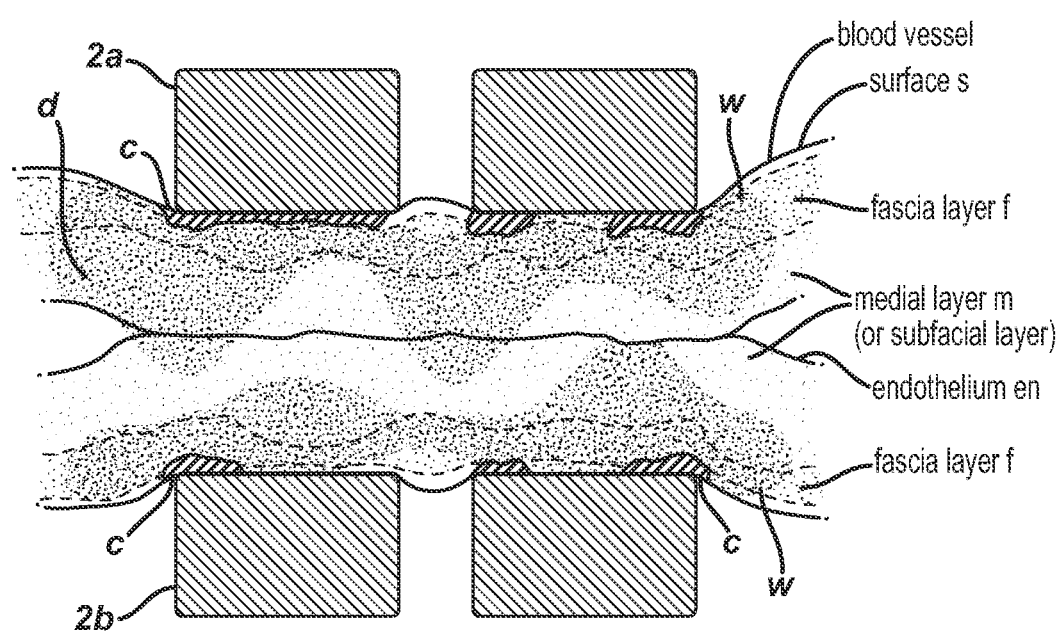
FIG. 1B illustrates representative weld effects of the bi-polar current flow of FIG. 1A.
Figure 2:
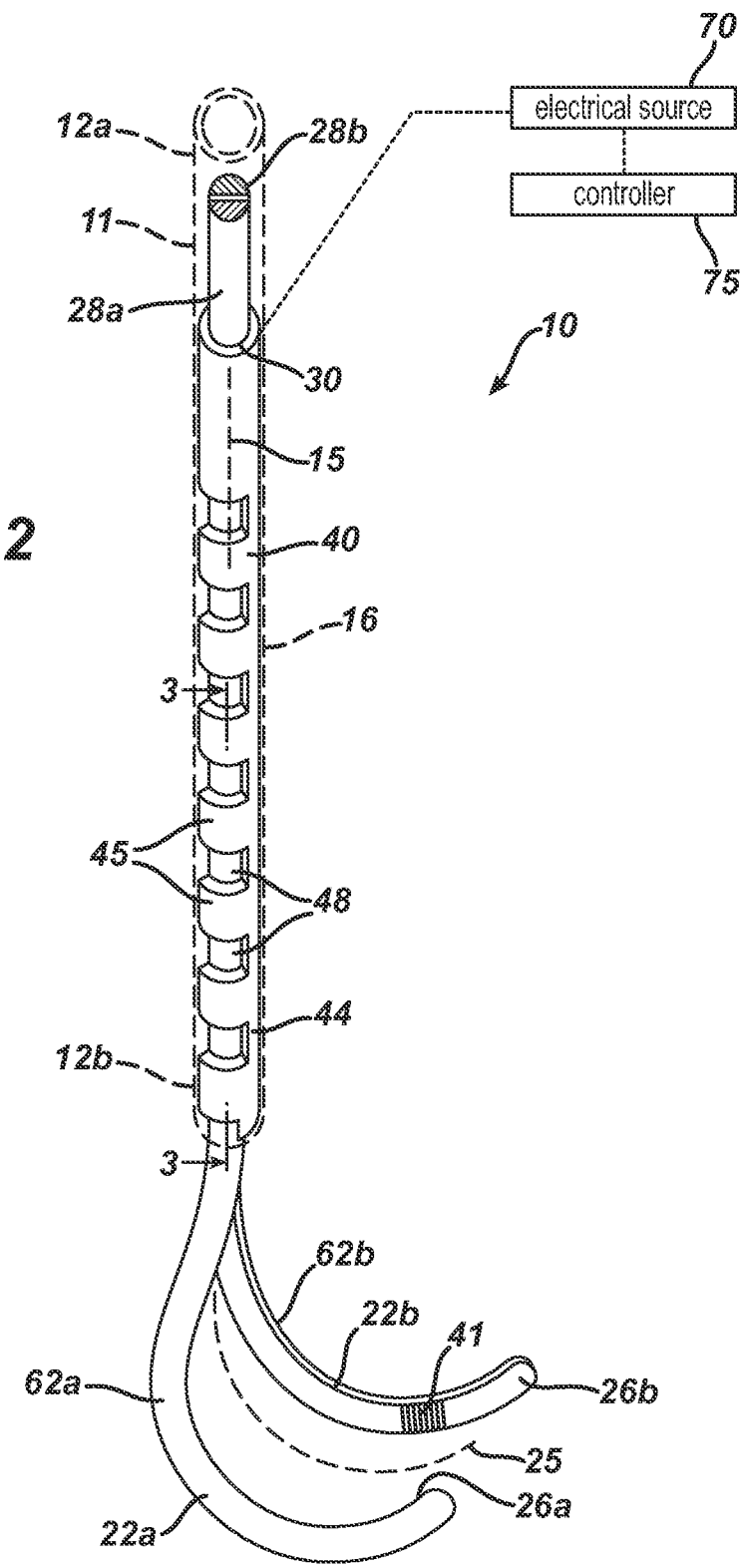
FIG. 2 is a view of an exemplary Type "A" working end corresponding to the present invention showing first and second jaw members extending from the distal end of an introducer body (phantom view), with a cooperating translatable extension member in a first non-extended position within the introducer body.

1. Type "A" working end for tissue transection. Referring to FIG. 2, the working end 10 of an exemplary Type "A" embodiment is shown that is adapted for electrosurgically transecting a volume of tissue from a patient's lung or other targeted structure while at the same time sealing the transected tissue margin. The working end 10 comprises an introducer body portion 11 (phantom view) that extends from a proximal body end 12a to a distal body end 12b along longitudinal axis 15. In the exemplary embodiment of FIG. 2, the introducer body 10 can have a cylindrical or oval cross-section and comprises a thin-wall tubular sleeve 16 that extends from any suitable handle (not shown). The diameter of sleeve 16 can range from about 5 mm. to 10 mm., although other diameter instruments fall within the scope of the invention. The handle may be any type of pistol-grip or other type of handle known in the art that carries an actuator lever or slide to extend the translatable member 40 over first and second jaws 22a and 22b as will be described below.

Figure 3:
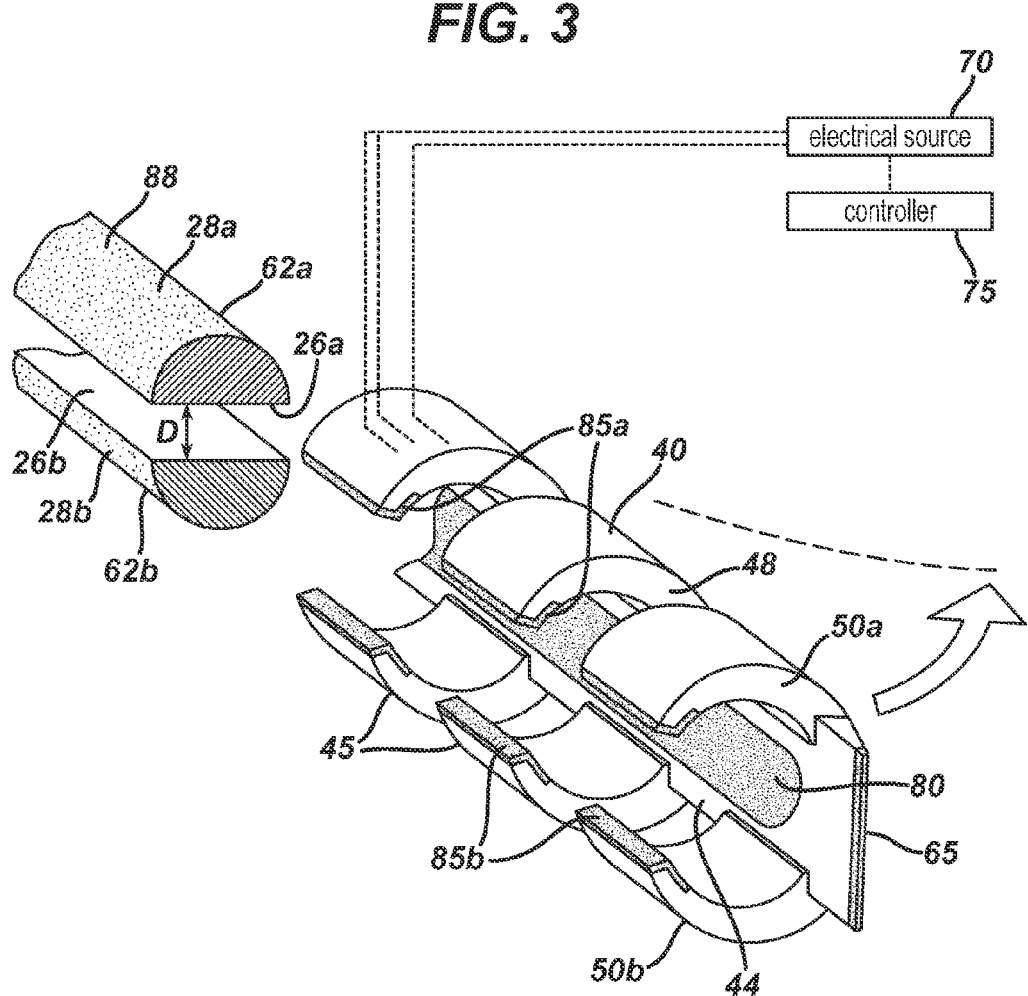
FIG. 3 is a perspective view of the proximal portions of the extending member that carry the paired jaws and a portion of the translatable member taken along line 3-3 of FIG. 2.

As can be seen in FIG. 2, the paired jaw members 22a and 22b are formed to extend substantially rigidly about a curved axis indicated 25 that is defined by the jaw's cooperating engagements surfaces 26a and 26b in the closed position when engaging tissues. FIGS. 2-3 show that the independent jaw members 22a and 22b comprise the distal portion of elongate extension rod members 28a and 28b that extend from the instrument handle. The extensionmembers 28a and 28b can have a cross-section ranging from about 0.05" to 0.20" and can have a flat surface so that the paired members can be slidably received by bore 30 in translatable member 40. The extension members and jaws 22a and 22b are formed of a suitable metal rod material with the flattened engagements surfaces 26a and 26b having serrations 41 another gripping surface for gripping tissue. It should be appreciated that curved portions of jaws 22a-22b can have any suitable radius or curve for transecting tissue of a selected dimension.

Of particular interest, FIGS. 3 and 4 illustrate a translatable member 40 that is adapted to perform multiple functions: (i) to provide a laterally-flexing cam mechanism that can slide over the curved jaws to thereby highly compress engagement surfaces 26a and 26b against opposing sides of the targeted tissue T; (ii) to contemporaneously transect the targeted tissue along a path p that is defined by the engagement axis 25 of the jaws, and (iii) in some embodiments, to carry electrode arrangements that can cooperate jaw electrodes to seal the margin of the transected tissue.

FIG. 3 shows a perspective view of translatable member 40 and illustrates the manner in which the member is flexible so as to bend laterally to slide over the curved jaw members 22a and 22b (see FIG. 2) while at the same time providing cam surfaces for moving the jaws to the closed tissue-engaging position from the open position. In this exemplary embodiment, the translatable member 40 can be fabricated from a metal tubular material with sections removed therefrom or can be fabricated by plastic injection molding. No matter the material, the component comprises a laterally-flexing backbone portion indicated at 44 that is connected to jaw-engaging sections 45 (collectively) that are spaced apart along the backbone and separated by cuts or scallops 48 (collectively).

It can easily be seen how the translatable member 40 can bend laterally as depicted by the arrow in FIG. 3 to follow the curves of jaws 22a-22b. More in particular, this embodiment shows that jaw-engaging sections 45 comprise upper and lower "c"-shaped portions or flanges 50a and 50b that define inner surfaces 52a and 52b for slidably engaging the jaws 22a and 22b about outward surfaces 62a and 62b of the jaws (FIG. 2). In this embodiment, the inner cam surfaces 52a-52b of translatable member 40 have a part-round cross-section to slidably cooperate with the rounded surfaces 62a-62b of the jaws, but it should be appreciated that any cooperating shapes are possible as long as the cam surfaces 52a-52b wrap partially (laterally) around the jaw members to insure that the "c"-shaped portions 50a-50b will track over the curved jaws as they compress the targeted tissue.

As can be seen in FIG. 3, the extension members and jaws 22a and 22b in the closed position define a dimension D between the engagement surfaces 26a and 26b which is selected as appropriate for engaging and compressing the targeted tissue, which is typically quite narrow and selected for the particular targeted tissue. In order to insure that the "c"-shaped portions 50a-50b of the translatable member 40 have sufficient strength to maintain their shape without flexing in order to compress the jaws over the targeted tissue, the cross-section of jaw-engaging sections 45 is made sufficiently thick or with any suitable reinforcing shown for additional strength.

Now turning to the electrosurgical functionality of the invention, FIG. 3 shows that distal termination 64 of the translatable member 40 carries an electrode cutting element indicated at 65. In the exemplary embodiment of FIG. 3, the translatable member 40 is of a molded non-conductive material and electrode 65 is coupled to electrical source 70 and controller 75 by electrical lead 76 that extends through backbone portion 44 of member 40. If the translatable member 40 is of a conductive metal, the distal cutting electrode 65 is insulated from the member as is known in the art, for example by providing an electrode carried over a thin insulated film backing.

Still referring to FIG. 3, it can be seen that translatable member 40 is further carries an electrode arrangement for sealing the tissue margin captured between the jaws 20a-20b. More in particular, member 40 has cooperating electrode surface portions 80 and 85a-85b that are exposed to contact the captured tissue: (i) at the transected medial tissue that interfaces the medial electrode 80, and (ii) at opposed exterior surfaces of the captured tissue that contacts the outboard electrodes 85a-85b, respectively (see FIG. 4C). For purposes of illustration, the exposed electrode surface portions 80 and 85a-85b are indicated in FIG. 3 to have a positive polarity (+) and negative polarity (−). These opposing polarity electrodes are, of course, spaced apart from one another and coupled to the electrical source 70 that defines the positive and negative polarities during operation of the instrument. The medial electrode 80 is coupled to electrical source 70 and controller 75 by lead 86 that extends through backbone portion 44 of the member. The outboard electrodes 85a-85b are similarly coupled to electrical source 70 and controller 75 by leads 87a and 87b. In the exemplary embodiment of FIG. 3, the extension members and jaw members 20a-20b have an insulative coating indicated at 88 so as to not provide a conductive path between the active electrodes.

Figure 4B:
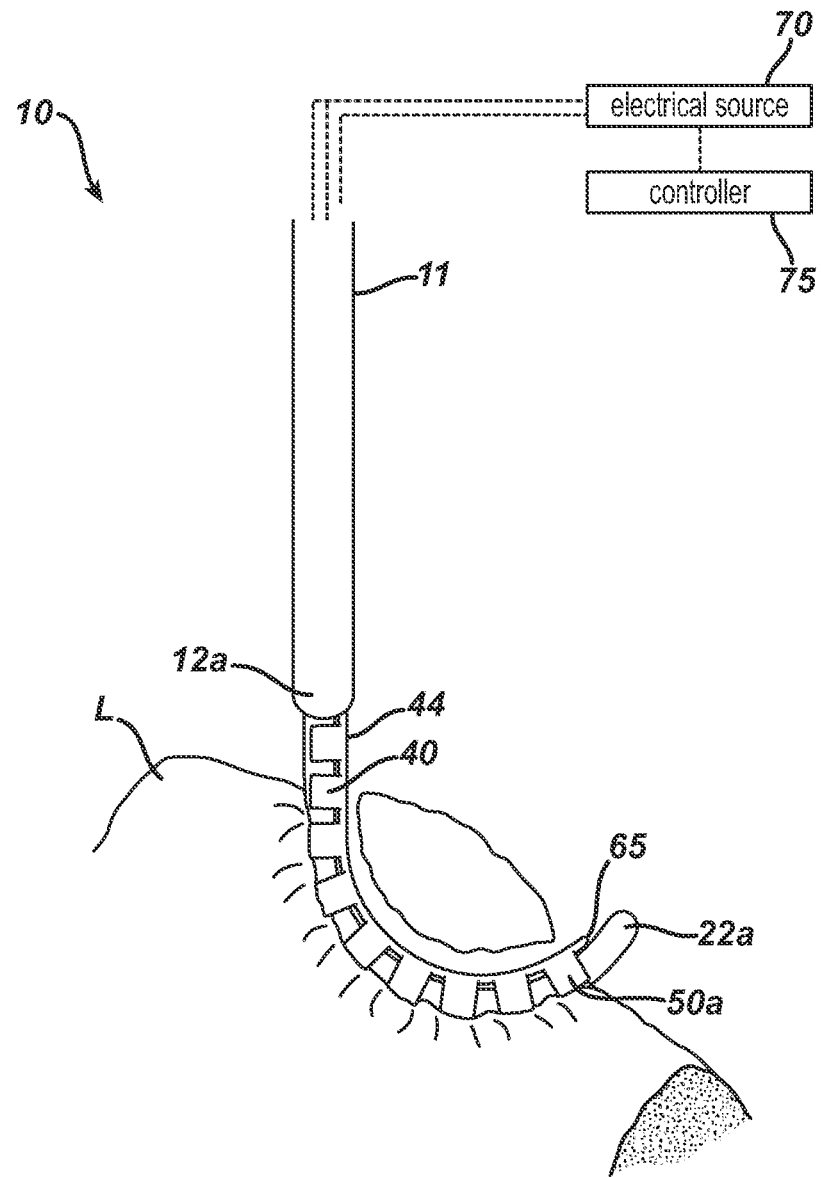

Now turning to FIGS. 4A-4C, the operation and use of the working end 10 of FIG. 2 in performing a method of the invention can be briefly described as follows. FIG. 4A depicts the working end being positioned over an edge of a patient's lung L or other body structure where the objective is to remove a tissue sample indicated at T. FIG. 4B shows the translatable member 40 being advanced from its non-extended (linear) position to its extended and curved distal position as it ramps over the tissue by advancing over the jaws members 20a-20b that compress the tissue just ahead of the advancing member 40. The laterally-outward portions of the translatable member 40 thereby slide over and engage the just-transected tissue margin m contemporaneous with cutting electrode 65 transecting the tissue. By this means, the tissue margin m is captured under high compression by the cooperating components of the working end 10. FIG. 4B also shows the tissue sample T being resected from the lung.

Figure 4C:
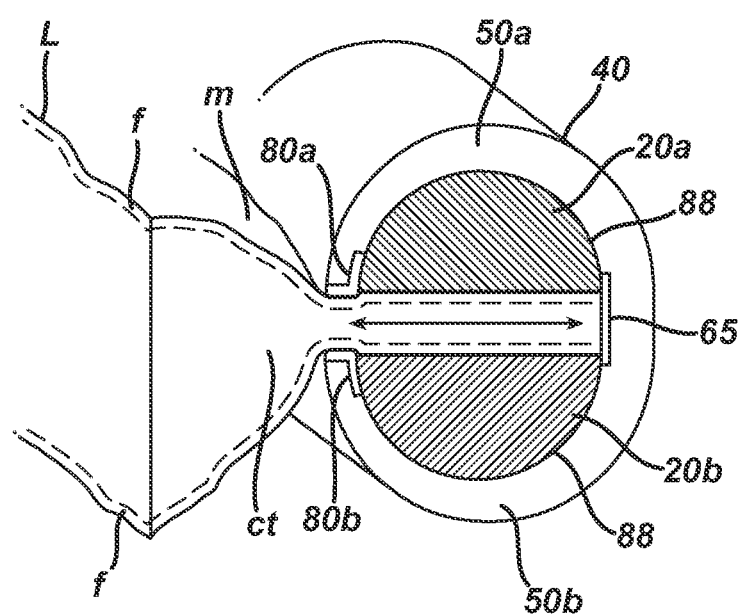

FIG. 4C depicts the tissue margin m captured between jaws members 20a-20b and upper and lower portions of the jaw-engaging sections 45 of member 40. The tissue margin m may be any soft tissue or anatomic structure of a patient's body. In this example, the tissue is shown with a surface or fascia layer indicated at f and medial tissue layers mt. FIG. 4C provides an illustration of one preferred manner of Rf current flow that causes a sealing or welding effect by the medial-to-surface bi-polar current flow (or vice versa) indicated by arrows A. It has been found that a substantially uniform weld can be created across the captured tissue margin by causing current flow from exposed medial electrode surface 80 to electrodes 85a and 85b. In other words, the sectional illustration of FIG. 4C indicates that a weld can be created in the captured tissue margin where proteins (including collagen) are denatured, intermixed under high compressive forces, and fused upon cooling to seal or weld the transected tissue margin. Further, the desired weld effects can be accomplished substantially without collateral thermal damage to adjacent tissues indicated at ct in FIG. 4C.

Another embodiment of the invention (not shown) includes a sensor array of individual sensors (or a single sensor) carried in any part of the translatable member 40 or the jaws 20*a*-20*a* that contact engaged tissue. Such sensors preferably are located either under an electrode or adjacent to an electrode for the purpose of measuring temperatures of the electrode or tissue adjacent to an electrode during a welding procedure. The sensor array typically will consist of thermocouples or thermistors (temperature sensors that have resistances that vary with the temperature level). Thermocouples typically consist of paired dissimilar metals such as copper and constantan which form a T-type thermocouple as is known in the art. Such a sensor system can be linked to feedback circuitry that together with a power controller can control Rf energy delivery during a tissue welding procedure. The feedback circuitry can measure temperatures at one or more sensor locations, or sensors can measure the impedance of tissue, or voltage across the tissue, that is engaged between the electrodes carried by the working end. The power controller then can modulate Rf delivery in order to achieve (or maintain) a particular parameter such as a particular temperature in tissue, an average of temperatures measured among multiple sensors, a temperature profile (change in energy delivery over time), a particular impedance level or range, or a voltage level as is known in the art.

Figure 5:
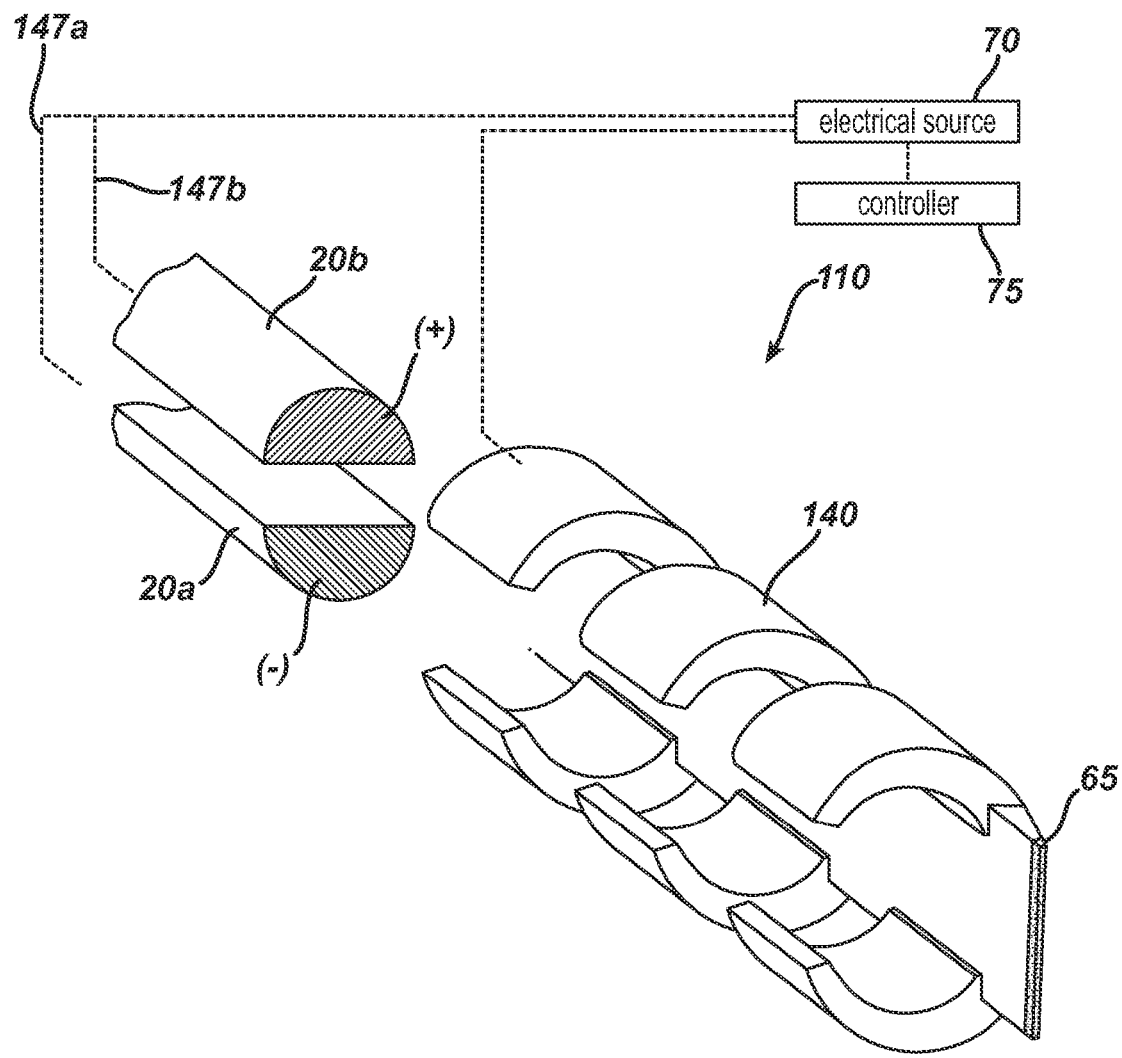
FIG. 5 is a view of the components of a Type "B" working end wherein the jaws and translatable member provides a different electrode arrangement for sealing tissue.

2. Type "B" working end for tissue transection. Referring to FIG. 5, components of a Type "B" working end 110 are shown that again are adapted for transecting and welding a tissue margin. This embodiment operates as described previously with translatable member 140 adapted to slide over the jaws 20*a* and 20*b* and again carries distal cutting electrode 65. However, in this embodiment, each jaw member 20*a* and 20*b* is coupled to electrical source 70 and controller 75 by electrical leads 147*a* and 147*b* to function as paired bi-polar electrodes with positive polarity (+) and negative polarity (−) indicated in FIG. 5. The paired jaw-electrodes themselves deliver Rf energy to the tissue which can be suitable for tissues that have substantially thin fascia layers and that have uniform collagenous content.

In another embodiment (not shown) the translatable member can carry at least one electrode as depicted in FIG. 3 to cooperate with the active electrode jaws of FIG. 5. The controller 75 then can multiplex the Rf current flow along different selected paths among spaced apart electrodes as described in co-pending U.S. patent application Ser. No. 09/792,825 filed Feb. 24, 2001 titled Electrosurgical Working End for Transecting and Sealing Tissue, now U.S. Pat. No. 6,533,784, which is incorporated herein by reference. While FIGS. 2-5 depict an exemplary embodiment that uses a high-voltage cutting electrode to transect tissue, it should be appreciated that the cutting element also can be a sharp blade member.

Figure 6:
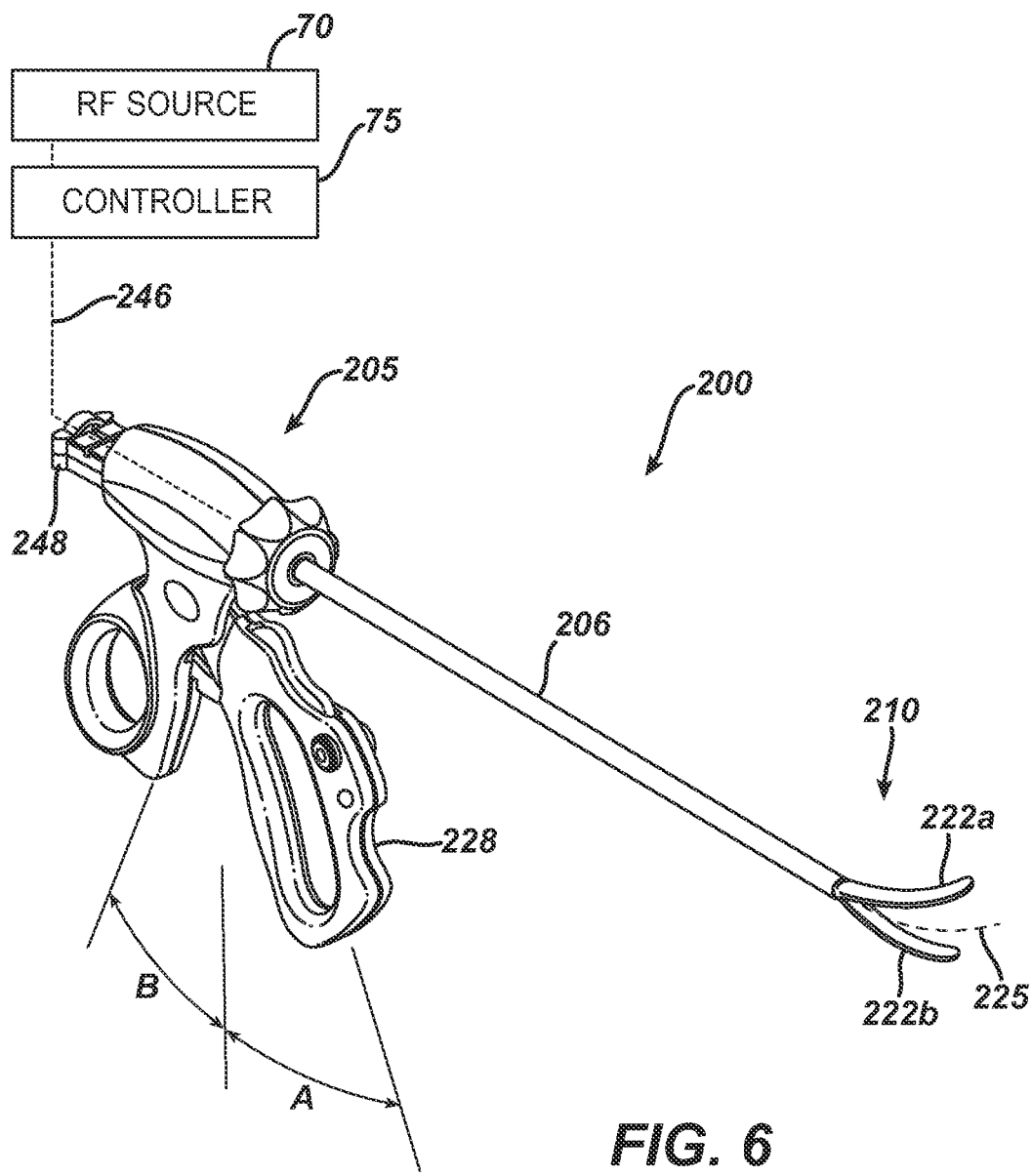
FIG. 6 is a perspective view of an alternative embodiment with a handle portion coupled to an elongated introducer member having a working end that carries a curved jaw structure.

FIG. 6 illustrates an alternative embodiment of instrument 200 for sealing and transecting tissue that includes handle 205 coupled to an elongate introducer member 206 that extends to working end 210A. The working end 210A again comprises an openable-closeable jaw assembly with curved first and second jaws 222*a* and 222*b* that close and engage tissue about a curved axis indicated at 225. The introducer 206 has a cylindrical or rectangular cross-section and can comprises a thin-wall tubular sleeve that extends from handle 205. The handle has lever arm 228 that is adapted to actuate and translate the translatable member 240 and an independent tissue cutting member 245 as will be described below. The Rf source 70 and controller 75 are coupled to the handle 205 by a cable 246 and connector 248.

The embodiment of FIG. 6 is configured differently than the previous embodiments in that the translatable member 240 for closing the curved jaw members 222*a* and 222*b* is not laterally flexible. However, the tissue-cutting member 245 is flexible thus allowing the blade's cutting path to follow a curve defined by the curved axis about which the jaws close. The linear stroke S of the translatable member 240 is shown in FIG. 7A-7C and FIGS. 8A-8B wherein the cam surfaces of translatable member 240 extend only over a proximal linear portion 249 of the jaws.

Figure 8A:
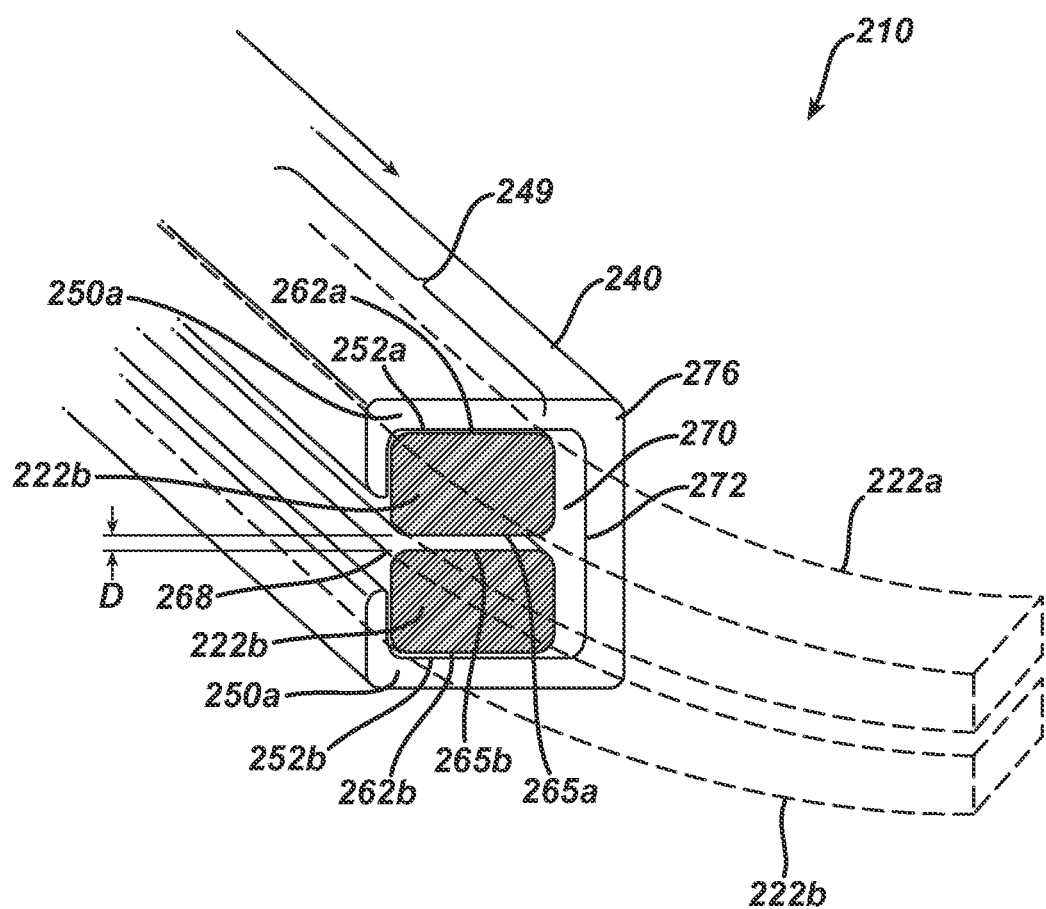
FIG. 8A is a perspective cut-away view of the working end of FIGS. 7A-7C in a jaw-closed position.

Turning to FIG. 8A, it can be seen that translatable member 240 again has upper and lower flanges or "c"-shaped portions 250*a* and 250*b* that define inner cam surfaces 252*a* and 252*b* for slidably engaging outward-facing surfaces 262*a*-262*b* of jaws 222*a* and 222*b*. The inner cam surfaces 252*a* and 252*b* of translatable member 240 can have any suitable profile to slidably cooperate with surfaces 262*a*-262*b* of the jaws. As can be seen in FIG. 8A-8B, the jaws 222*a* and 222*b* in the closed position define a gap or dimension D between the jaws' energy-delivery surfaces 265*a* and 265*b* which equals from about 0.0005" to about 0.005" and preferably between about 0.001" about 0.002". The edges 268 of the energy-delivery surfaces 265*a* and 265*b* are rounded to prevent the dissection of tissue. A space or channel 270 is provided between the jaws and transverse surface 272 of translatable member 240 to accommodate the sliding movement of tissue-cutting member 245.

Figures 7A, 7B, 7C:
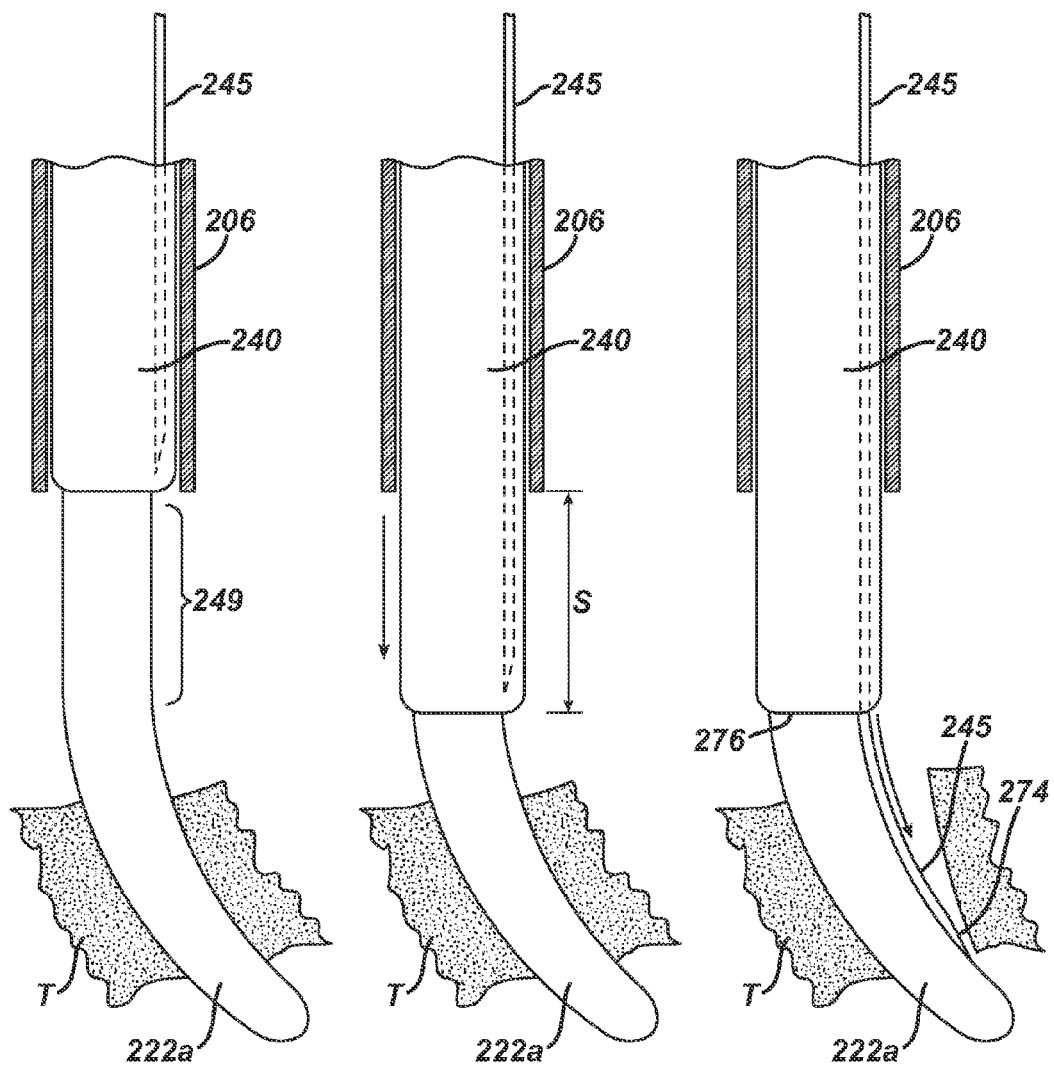
FIGS. 7A-7C are plan views of the working end of the instrument of FIG. 6 in different stages of operation.

FIGS. 7A-7C illustrate the combined actuation of translatable member 240 for closing the curved jaw members and the actuation of tissue-cutting member 245 for transecting the engaged and sealed tissue. FIG. 7A depicts a view from above of jaws 222*a* and 222*b* engaging tissue indicated at T before the jaws are closed. FIG. 7B illustrates the translatable member 240 being advanced from its non-extended position to an extended position (or stroke S) as inner cam surfaces 252*a* and 252*b* of translatable member 240 advance over the outer surfaces of linear section 249 of the jaws (see FIG. 8A). The actuation of translatable member 240 is caused by moving lever arm 228 over the range of motion indicated at A in FIG. 6.

FIG. 7C illustrates the tissue-cutting member 245 with a sharp blade edge 274 being advanced from a non-extended position to its extended position to cut the engaged tissue T. As can be seen in FIG. 7C and 8B, the blade edge 274 advances beyond the distal end 276 of translatable member 240. The tissue-cutting member 240 is a thin flexible metal that allows it to flex and follow the curvature of the jaws. The actuation of tissue-cutting member 240 is caused by moving lever arm 228 over the range of motion indicated at B in FIG. 6.

In a method of use, the application of electrosurgical energy to the engaged tissue can occur contemporaneously with jaw closure and advancement of cutting member 245, or after closing the jaws. The controller can be programmed to deliver energy automatically upon advancement of the cutting member 245 or the system can be provided with an independent on-off footswitch for energy delivery.

Figure 9A:
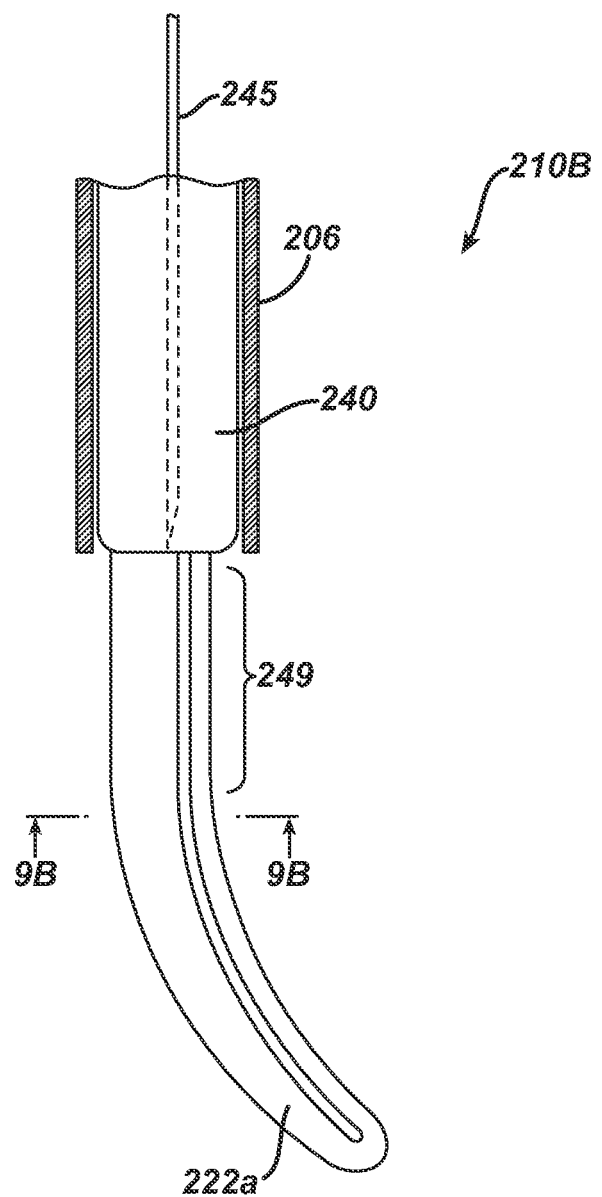
FIG. 9A is a plan view of an alternative embodiment of working end that carries a curved jaw structure.
Figure 9B:
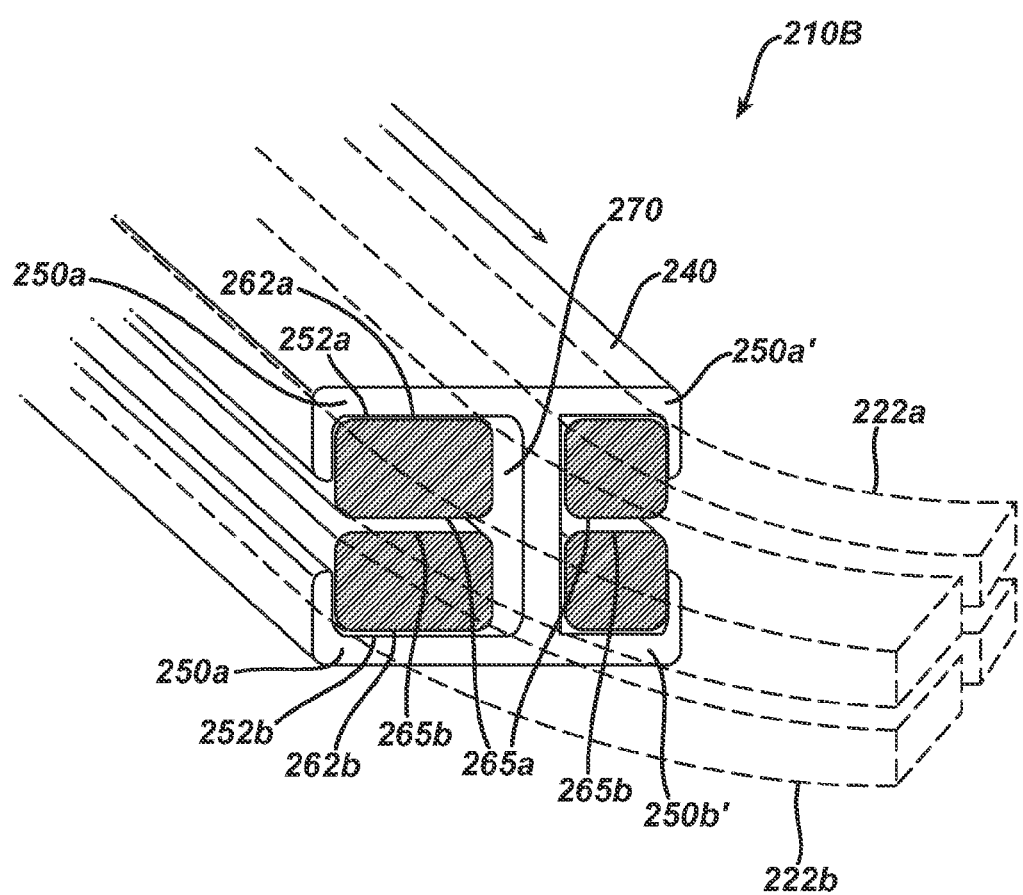
FIG. 9B is a cut-away view of the working end of FIG. 9A.

FIGS. 9A-9B illustrate an alternative working end 210B for sealing and transecting tissue that again includes curved first and second jaws 222*a* and 222*b* that close and engage about a curved axis. This embodiment is configured for sealing both sides of transected tissue and thus has energy-delivery surfaces 265*a* and 265*b* that extend on both sides of channel 280 in the jaws that slidably accommodates the transverse element 282 of the translatable member 240. As can be seen in FIG. 9B, the cross-section of translatable member 240 has a configuration similar to an I-beam. Flange portions 250*a* and 250*a*' extend across the upper portion of translatable member 240 and flange portions 250*b* and 250*b*' extend across the lower portion of the translatable member 240. The I-beam configuration for closing electrosurgical jaws under high compression is described in co-pending application Ser.

No. 10/032,867 and Ser. No. 10/308,362 which are incorporated herein by this reference. As can easily understood from FIGS. 9A-9B, the translatable member 240 can be translated axially over the linear portion 249 of jaws 222a and 222b until it reaches the limit of its stroke to close the jaws. Thereafter, the blade member 245 is advanced to transect the engaged tissue.

Now turning FIGS. 10-14, various embodiments of electrosurgical energy-delivery surfaces 265a and 265b are shown schematically. Each embodiment can be used to achieve a somewhat different tissue effect in the jaw structures of FIGS. 7A-8B and 9A-9B. For convenience, FIGS. 10-14 illustrate first and second jaws 222a and 222b of the type described in the text with reference to FIGS. 8A-8B, although it can be easily understood that the jaws of FIGS. 10-14 can have a channel 280 as in the embodiment of FIGS. 9A-9B for receiving an I-beam member.

Figure 10:
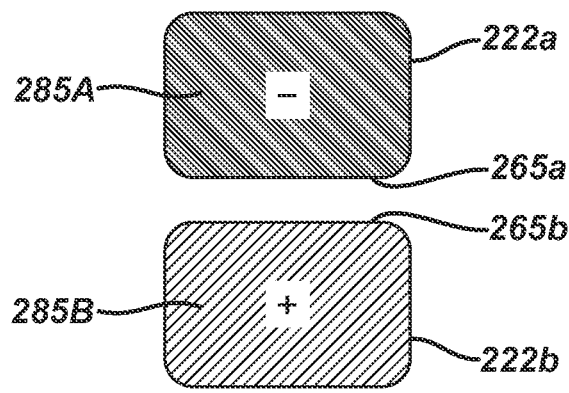
FIG. 10 is a schematic sectional view the first and second jaws of the working end of FIGS. 7A-7C and FIGS. 8A and 8B illustrating an exemplary configuration of electrosurgical energy-delivery surfaces.

FIG. 10 illustrates a working end with first and second jaws 222a and 222b wherein the electrosurgical energy-delivery surfaces 265a and 265b comprise surface portions of first and second conductive bodies 285A and 285B having opposing polarities indicated as positive polarity (+) and negative polarity (−). The first and second conductive bodies 285A and 285B are coupled by electrical leads to Rf source 70 and controller 75 as described above. In this embodiment, the inner surfaces of translatable member 240 are coated with an insulator layer to prevent the translatable member 240 from forming a conductive path between the opposing poles.

Figure 11:
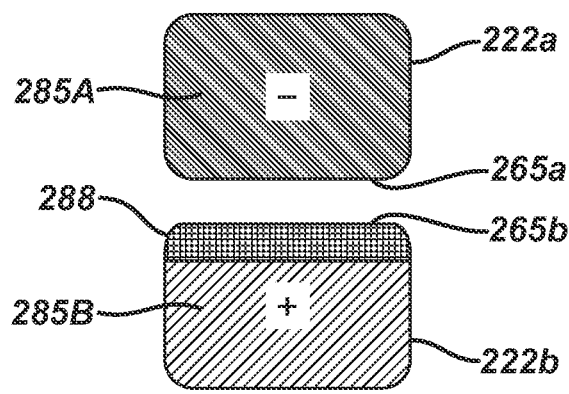
FIG. 11 is a schematic sectional view of alternative first and second jaws similar to FIG. 10 with a different configuration of electrosurgical energy-delivery surfaces.

FIG. 11 illustrates an alternative embodiment wherein the first and second jaws 222a and 222b again include first and second conductive bodies 285A and 285B, respectively. A first electrosurgical energy-delivery surface 265a again comprises a surface portion of conductor or electrode 285A. The second energy-delivery surface 265b comprises a layer or body 288 of a pressure-sensitive resistive material that extends entirely across the jaw surface. The polymeric material has a pressure-resistance profile wherein increased pressure reduces the resistance of body 288 as described in co-pending U.S. patent application Ser. No. 10/032,867 and Ser. No. 10/308,362. In use, the engagement of tissue will cause pressure against body 288 which will thereafter cause increased localized current flows through the body 288 and within adjacent the tissue wherein engagement pressure is the highest. In localized areas where engagement pressure is lower, less current will flow through that portion of body 288 and the adjacent engaged tissue. As tissue parameters such as tissue impedance change during the tissue sealing process, the dehydration of tissue will reduce its cross-section thereby reducing engagement pressure which thereby reduces current flow through the tissue. In this embodiment, the pressure-sensitive variable resistive body 288 can be understood to be a load-carrying material or body, which also has the ability to reduce arcing and tissue desiccation at the energy-delivery surface 265a.

The schematic view of FIG. 11 also can be use to illustrate related embodiments wherein first energy delivery surface 265a comprises a surface portion of conductive body or electrode 285A indicated as negative polarity (−). The second conductive body 285B has a surface layer or body 288 of a load-carrying material that comprises another type of partially resistive material in second surface 265b. Such a body 288 includes partially resistive materials such as a positive temperature coefficient of resistance material (PTCR) or a fixed resistance material, as disclosed in co-pending U.S. patent application Ser. No. 10/032,867, Ser. No. 10/308,362 Ser. No. 10/032,867 and Ser. No. 10/291,286. The use of such a load-carrying body 288 has the ability to reduce arcing at the energy-delivery surface 265a, and further provide passive (non-ohmic) heating of engaged tissue as the material heats from internal resistance and from being heated by adjacent ohmically-heated tissue.

Figure 12:
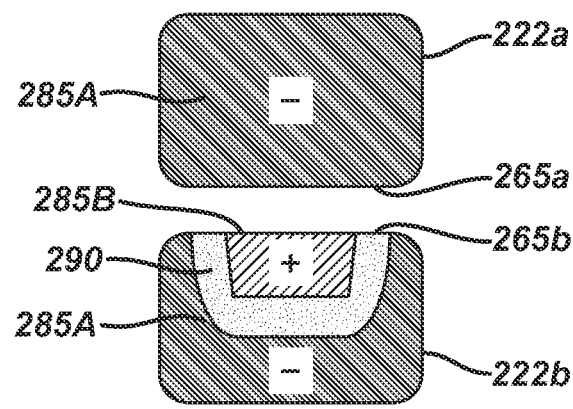
FIG. 12 is a schematic view of alternative of first and second jaws with another configuration of electrosurgical energy-delivery surfaces.

FIG. 12 is a schematic view of an alternative embodiment wherein first energy-delivery surface 265a comprises a surface portion of conductive body or electrode 285A indicated as a negative polarity (−). The second energy delivery surface 265b includes another portion of negative polarity (−) electrode 285A in contact with a partially resistive load-carrying material indicated at 290. Spaced apart from negative polarity (−) electrode 285A is an opposing polarity (+) electrode 285B that is also in contact with the partially resistive load-carrying material 290. Thus, the partially resistive load-carrying material 290 is intermediate (and in contact with) the opposing polarity electrodes 285A and 285B. The partially resistive load-carrying material 290 preferably is a PTC material, a fixed resistance material, or a pressure sensitive material, as described above and in the previously identified related applications. Such load-carrying bodies 290 can reduce arcing and reduce tissue desiccation to enhance the creation of a high strength seal in the engaged tissue.

Figure 13:
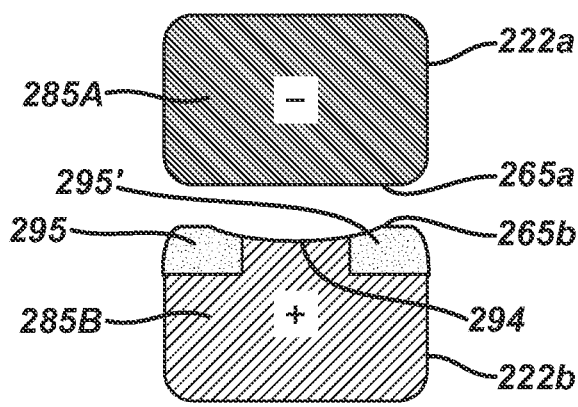
FIG. 13 is a schematic view of alternative of first and second jaws with another configuration of electrosurgical energy-delivery surfaces

FIG. 13 illustrates an alternative working end embodiment wherein first and second jaws 222a and 222b again include first and second conductive bodies or electrodes 285A and 285B that are exposed in the respective energy-delivery surfaces 265a and 265b. In this embodiment, the central portion 294 of surface 265b is concave or recessed relative to lateral body portions 295 and 295' that comprise a load-carrying material consisting of a PTCR material as described above. In this embodiment, the jaw surfaces can be compressed together under extremely high pressures which are useful for sealing tissue and any inadvertent contact of surfaces 265a and 265b will not cause a short since contact of any region of the PTCR body 295 and 295' with the opposing jaw will rapidly heat the contact point of the PTCR material and cause its local resistance to increase until that local portion is non-conductive. It can be understood that the central recessed portion 294 of surface 265b is thus prevented from contacting the opposing polarity electrode of the opposing jaw no matter how high the compression of tissue.

Figure 14:
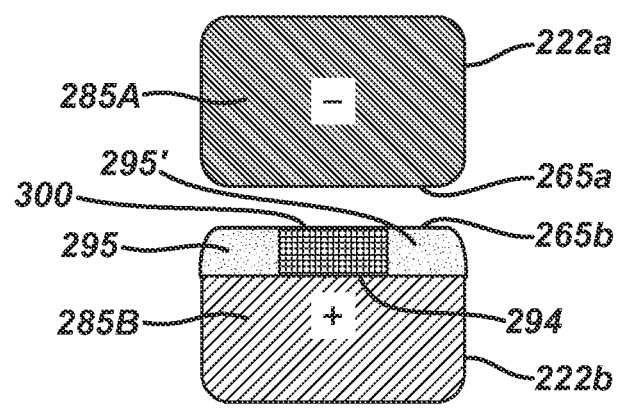
FIG. 14 is a schematic view of alternative of first and second jaws with yet another configuration of electrosurgical energy-delivery surfaces

FIG. 14 illustrates another embodiment wherein first and second jaws 222a and 222b again include first and second conductive bodies or electrodes 285A and 285B. In this embodiment, the first energy-delivery surface 265a is an exposed surface of electrode 285A but also can be carry any of the configurations of surfaces with load-carrying materials described above. The second surface 265b has a central body portion 300 of a pressure-sensitive resistive material as described previously in the text relating to FIG. 11. The central polymeric body 300 is surrounded by lateral body portions 295 and 295' that comprise a load-carrying material consisting of a PTCR material as described above in FIG. 13. In use, the jaw surfaces can be compressed together and high pressures will cause the central polymeric body 300 to compress and deliver current therethrough to the tissue. The PTCR body portions 295 and 295' will insure that any inadvertent contact of surfaces surface 265a and 265b will not cause a short circuit as described in the embodiment of FIG. 13. In this embodiment, the pressure-sensitive variable resistive body 300 will locally modulate current flow in tissue and prevent the possibility of arcing and tissue desiccation at the energy-delivery surfaces.

Although particular embodiments of the present invention have been described above in detail, it will be understood that this description is merely for purposes of illustration. Specific features of the invention are shown in some drawings and not in others, and this is for convenience only and any feature may be combined with another in accordance with the invention. Further variations will be apparent to one skilled in the art in light of this disclosure and are intended to fall within the scope of the appended claims.

What is claimed is:

1. A surgical instrument, comprising:
   an elongate introducer having a working end including openable-closeable first and second jaw members having curved distal portions that define a curved tissue-engaging axis;
   a flanged member that is slidably carried by the introducer, the flanged member moveable between a first non-extended position and second extended position wherein flanges slidably engage the jaw members to move the jaws from an open position to a closed position; and
   a flexible tissue-cutting member slidably carried by the introducer, the tissue-cutting member moveable between a first non-extended position and a second extended position that extends distally beyond the flanged member and flexes.

2. The surgical instrument of claim 1 wherein the flanged member in configured with laterally-extending flanges.

3. The surgical instrument of claim 1 wherein the flanges slidably engage outwardfacing surfaces of the jaw members.

4. The surgical instrument of claim 1 wherein the tissue-cutting member includes a blade edge.

5. The surgical instrument of claim 1 wherein the tissue-cutting member includes an electrode.

6. The surgical instrument of claim 1 wherein at least one jaw member includes an electrosurgical energy-delivery surface for delivering energy to tissue.

7. The surgical instrument of claim 6 wherein the electrosurgical energy-delivery surface includes first and second polarity electrodes.

8. The surgical instrument of claim 6 wherein the electrosurgical energy-delivery surface includes a body having a positively or negatively sloped temperature-resistance profile.

9. The surgical instrument of claim 6 wherein the electrosurgical energy-delivery surface includes a body that exhibits a pressure-resistance profile wherein resistance decreases with pressure.

10. The surgical instrument of claim 6 wherein the electrosurgical energy-delivery surface includes a body having a fixed resistance.

11. The surgical instrument of claim 6 wherein the electrosurgical energy-delivery surface of the first jaw member includes a first body comprising an electrode and a second body comprising a load-carrying material that is partially resistive.

12. The surgical instrument of claim 11 wherein the first body and the second body are in contact in the energy-delivery surface.

13. The surgical instrument of claim 6 wherein the electrosurgical energy-delivery surface of the first jaw member includes a first body comprising spaced apart opposing polarity electrodes and a second body comprising a load-carrying material that is partially resistive.

14. The surgical instrument of claim 13 wherein the first body and the second body are in contact in the energy-delivery surface.

15. The surgical instrument of claim 1 wherein the flanged member comprises a plurality of axially-extending elements.

16. The surgical instrument of claim 15 wherein the plurality of axially-extending elements are coupled by a flexible hinge joint.

17. The surgical instrument of claim 15 wherein the plurality of axially-extending elements are coupled by at least one flexible cable.

* * * * *